United States Patent [19]

Sturrock et al.

[11] Patent Number: 5,374,892
[45] Date of Patent: Dec. 20, 1994

[54] DIGITAL ELECTROCHEMICAL INSTRUMENT WITH BACKGROUND COMPENSATION

[75] Inventors: Peter E. Sturrock, Doraville; Gerald E. O'Brien, Dunwoody, both of Ga.

[73] Assignee: Georgia Tech Research Corporation, Atlanta, Ga.

[21] Appl. No.: 26,440

[22] Filed: Mar. 4, 1993

[51] Int. Cl.⁵ ............................................. G01N 27/00
[52] U.S. Cl. .................................... 324/720; 324/444;
324/693; 324/715; 204/407; 204/153.1;
422/82.01; 436/149
[58] Field of Search ............... 324/439, 444, 693, 705,
324/715, 717, 720; 204/406, 407, 153.1;
422/82.01, 82.02, 82.03; 436/149, 806

[56] References Cited

U.S. PATENT DOCUMENTS

| | | | |
|---|---|---|---|
| 4,628,463 | 12/1986 | Sturrock et al. | 364/497 |
| 4,682,113 | 7/1987 | Barben | 324/441 |
| 4,683,435 | 7/1987 | Blades | 324/442 |
| 4,691,168 | 9/1987 | Dzula | 324/439 |
| 4,814,281 | 3/1989 | Byers | 436/150 |
| 4,888,484 | 12/1989 | Harvey | 250/343 |
| 4,979,823 | 12/1990 | Mohr et al. | 356/307 |
| 5,096,807 | 3/1992 | Leaback | 435/6 |
| 5,220,514 | 6/1993 | John | 324/705 X |

Primary Examiner—Kenenth A. Wieder
Assistant Examiner—Glenn W. Brown
Attorney, Agent, or Firm—Deveau, Colton & Marquis

[57] ABSTRACT

An instrument and method for measuring chemical properties, the instrument having electrodes suitable for immersion in a chemical solution. A voltage source and a current-sensing circuit are connected to the electrodes to measure the current produced in the solution in response to a voltage applied to the electrodes to determine a value of the chemical in the solution. The instrument and method further include background compensation for offsetting the value of the analyte by an amount which is reflective of the background value of the solution. The background value is stored in an internal memory of the instrument so that when new experimental measurements are taken, the measurements are immediately offset by the background portion of the new experimental measurements. This allows operation of the instrument at high gain levels, resulting in a broad dynamic range and greater useful precision in the output signal.

17 Claims, 9 Drawing Sheets

DIGITAL ELECTROCHEMICAL INSTRUMENT WITH BACKGROUND COMPENSATION

BACKGROUND OF THE INVENTION

1. Field of the Invention

The invention relates generally to the use of measuring instruments for chemical analysis and more specifically to the use of an instrument which uses the voltage and current characteristics of a sampling of a solution to determine the concentrations of various materials in the solution, i.e., a voltammetric instrument.

2. Description of the Related Art

A wide variety of techniques and devices are currently used to analyze the concentrations of various analytes in a solution. One such technique is voltammetry. Voltammetry is an electrochemical method for quantitative and qualitative analysis based on the relationship between a changing applied voltage and the resulting current through the solution being analyzed.

Like other chemical analysis techniques, voltammetry of solutions causes a background value (signal) upon which the response of the analyte of interest is superimposed. If the technique employed entails a systematic change in a controlled parameter such as wavelength or electrode potential, generally there is a different background value at each value of the controlled parameter, i.e., a background curve.

U.S. Pat. No. 4,628,463 to Starrock et al., for RAPID-SWEEP ELECTROCHEMICAL DETECTOR FOR CHEMICAL ANALYSIS OF FLOW STREAMS, discloses a data acquisition system with some ability to obtain accurate response peaks. However, the system is limited at low analyte concentrations by the background signal.

For many years, a technique known as background subtraction has been used to correct the measured values after data acquisition. In a typical background subtraction technique, raw data is collected with a measuring instrument, converted from analog-to-digital form, and passed to a digital computer, wherein the computer can subtract a previously or subsequently measured background value from the present measurement. While background subtraction is a useful approach, it is not adequate when the background curve changes over a wide range and the analyte response, i.e., the response of interest, is small in comparison to the change in the background. In such a situation, it has been necessary to operate the instrument or measuring device at low sensitivity, and the analyte response is then so small that it cannot be measured with adequate precision, if it can be detected at all.

This problem is especially troublesome in digital instruments in which an analog-to-digital converter (ADC) is used to convert the signal to a digital value to make it compatible with a computer. In such cases, the dynamic range of the instrument is limited by the number of bits of the ADC and possibly by the number of bits of the computer bus and processor. For example, a 12-bit ADC has only 4096 response levels (i.e., levels of precision). Almost all of these levels might be used by the changing background curve (the background value), and only a very few bits (levels) of precision might be used for the small analyte response. Thus, the measured analyte response is poorly defined and imprecise.

One way to address this situation is to use an ADC with more bits. However, this solution can be very costly and can inconveniently require a longer computer word (data) format, resulting in slower processing times and the requirement of more computer memory for storage capacity.

Thus, it can be seen that a need yet exists for a voltammetric instrument with a large dynamic range, without requiting the use of a larger data format. It is to the provision of such that the present invention is primarily directed.

SUMMARY OF THE INVENTION

Briefly described, the present invention comprises an instrument for measuring chemical properties, the instrument having at least two electrodes, each electrode having one end which is suitable for immersion in a chemical solution. The instrument includes a voltage source and a current sensing circuit. The electrodes are connected to the voltage source, while the current sensing circuit measures the current produced in the solution, in response to the voltage applied, to determine a value of the analyte in the solution. The instrument further comprises background compensation means for offsetting the measured value of the analyte by an amount which is reflective of the background value of the solution. The background value is stored in an internal memory of the instrument so that when new experimental measurements are taken, the measurements are immediately offset by the background portion of the new experimental measurements.

By offsetting the measurement directly in the instrument, before it would be passed to an external computer device through an analog-to-digital converter (ADC), the instrument can be operated at high gains, resulting in a broad dynamic range and greater useful precision in the output signal. This allows the instrument to attain high resolution measurements of the analyte of interest even when the analyte response is small in comparison to the background value which may vary over a wide range of values.

In another preferred form the present invention comprises a method of measuring a concentration of analyte in a solution, comprising the steps of measuring a background value of the solution with a measuring instrument, storing the background value in the measuring instrument, and determining the concentration of analyte in the solution by measuring a gross signal of the analyte and offsetting, in the measuring instrument, the gross signal by the background value. The method of the present invention may further include the step of scaling a multitude of stored background values so as to provide for background compensation of new experimental measurements at increased amplification, thus achieving highly sensitive and precise electrochemical analysis.

Accordingly, it is an object of the present invention to provide a means and method for high resolution chemical analysis in the presence of a background value.

It is another object of the present invention to provide a means and method for chemical analysis which is effective even in the presence of a background value which changes over a wide range.

A further object of the present invention is to provide a means and method for chemical analysis which is effective even when the analyte response is small in comparison to the change in the background value.

An additional object of the present invention is to provide a device and method which is effective for electrochemical analysis over a broad dynamic response range.

Still another object of the present invention is to provide a highly reliable and accurate means and method for electrochemical analysis which has high signal-to-noise ratios.

Yet another object of the present invention is to provide a means and method for electrochemical analysis which is fast, accurate, inexpensive, and easy to use.

These and other objects, features, and advantages of the present invention will become better understood to those skilled in the art when the following description and appended claims are read in conjunction with the attached drawing figures, wherein like reference numerals correspond to like parts throughout the several views.

DETAILED DESCRIPTION OF THE INVENTION

Figure 1A:
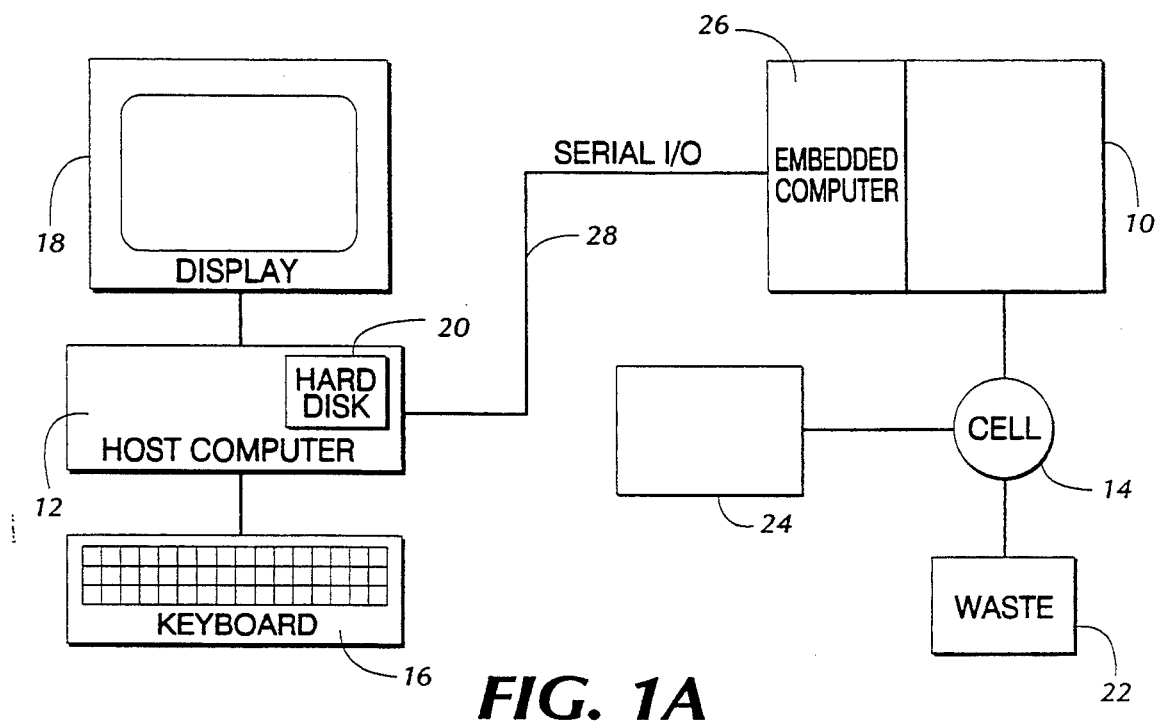
FIG. 1A is a functional block diagram of a preferred embodiment of a device according to the present invention.

An electrochemical detection system incorporating the present invention is shown in FIG. 1A, which is designed to perform voltammetric experiments on flowing streams and comprises the digital instrument indicated generally by the reference character 10, an associated host computer 12, and an electrode stand and flow cell indicated generally by the reference character 14. Flow cell 14 is shown in association with a flow stream source 24 comprising a pump, an injector, and a discharge (not shown) which discharges analyte through the flow cell 14 and ultimately to waste 22. Host computer 12 is a standard type personal computer and provides operator interface via keyboard 16, graphics display 18, and storage of data and programs via hard disk 20. The digital instrument 10 is linked to host computer 12 by a standard serial link 28, preferably fitted with RS-232 connectors, and includes a processor 26, chosen here to be an 80186 processor. Graphics display 18 permits one to observe the progress of an experiment in a qualitative and quantitative manner. Graphics display 18 indicates analyte response magnitudes for each potential during an experiment, thus enabling the operator to see results as they are acquired.

Important applications for the invention are as a detector for High-Performance Liquid Chromatography (HPLC), and for Flow Injection Analysis (FIA) and for process-control applications. However, the present invention may be used to perform traditional voltammetry in unstirred solutions. FIG. 1A illustrates an embodiment of the present invention associated with a flow stream source or flowing stream 24. The primary requirement for voltammetry in flowing streams is the ability to make rapid, repetitive voltammetric sweeps and to store the pertinent information from these sweeps for subsequent analysis. This requirement alone makes a computer-based instrument mandatory. The use of a computer-controlled instrument makes possible a variety of voltammetric techniques simply by changing the software.

Figure 1B:
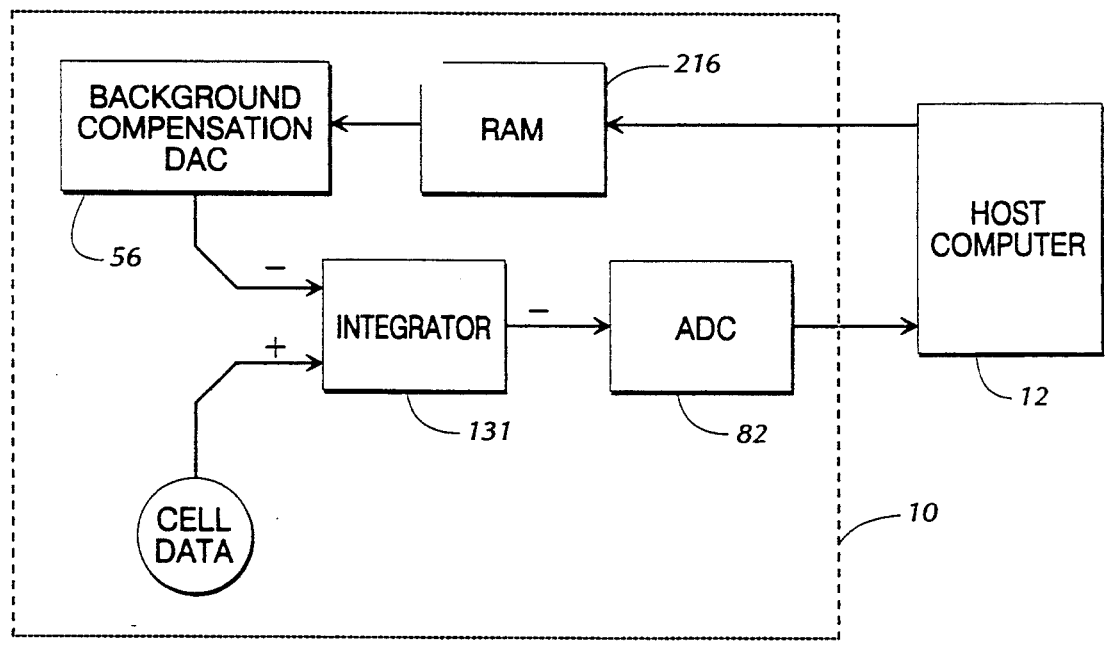
FIG. 1B is a functional block diagram of a portion of the device of FIG. 1A.

Referring now more specifically to FIG. 1B, an overview of the function and operation of the background compensation scheme according to the present invention is depicted. The details of various components and functions depicted in FIG. 1B are explained in more detail subsequently in this specification. As shown, the digital instrument 10 is connected with the host computer 12 for two-way communication. The general scheme of background compensation according to the present invention is that background values from the cell are provided to the integrator 131 which outputs the integrated value to the analog-to-digital converter (ADC) 82. In doing so, the integrator 131 inverts the signal. The output from the analog-to-digital converter 82 is transferred to the host computer 12. Four "sweeps" of data for background values are up-loaded to the host computer 12 with the background compensation turned off. The four background values at each point are arithmetically added in the host computer to create a sum and the sums are stored in RAM 216 in the instrument 10. When a sum is retrieved by the 80186 microprocessor in the instrument 10 and converted from digital format to analog format by the background compensation DAC 56, it loses the right-most two bits of information, since the DAC 56 is a 16-bit converter with its two right-most bits "tied down" (disabled). The effect then of summing the four sweeps in the host computer and converting the sum in a manner that drops the two right most bits of information is very nearly equal to an averaging of the four sweeps (note, that the 4's column becomes the 1's column, and so on, as the 16 bit information is squeezed through a 14-bit converter in this manner).

In subsequent data collection cycles, the microprocessor on the instrument 10 simultaneously controls the updating or sampling of the cell data with the updating or retrieval of the background value and these two values are fed in to the integrator 131 simultaneously. In other words, every time that the cell data is updated (sampled), simultaneously the background value is fed from RAM 216 through DAC 56 to the integrator 131 as well. By feeding back through this loop in this manner, the value coming through the background compensation DAC 56 is negative as depicted in FIG. 1B and can be simply added to the positive value of the measured value of the analyte with integrator 131 to obtain a net difference. Of course, the integrator 131 is an inverting integrator so that as the sum is fed back around through RAM 216 and DAC 56, a negative value is being integrated. This has the effect of offsetting the voltage corresponding to the measured current in the cell by the amount of the average background value voltage. What is not shown in FIG. 1B, and which is shown in more detail in FIG. 2A, is that the electrodes in the cell detect current and that the current is then converted into a voltage which is then in turn fed to the integrator 131.

The output from the integrator 131 when used in conjunction with the background compensation values stored in RAM 216, is passed to the analog-to-digital converter 82 and represents a compensated value of the analyte which has been offset from its raw value or absolute value by an amount equal to the background value. This allows the full range of the analog-to-digital converter 82 to be applied against the "signal portion", without usurping any of that range for background value. Thus, greater precision and more detailed information about the analyte is passed through the analog-to-digital converter 82 to the host computer 12 for storage and subsequent analysis and manipulation. This greatly improves the performance and effectiveness of such an instrument.

Figure 2A:
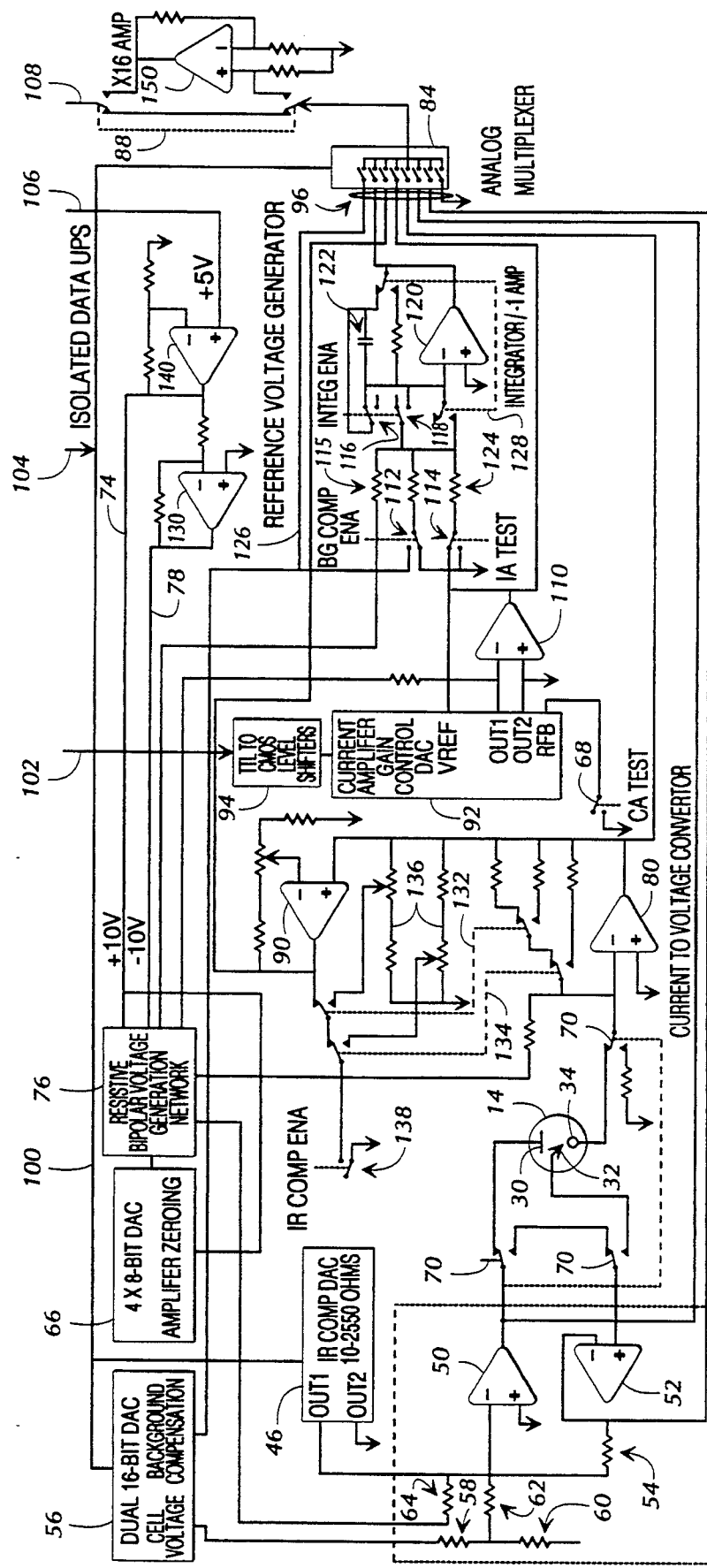
FIGS. 2A, 2B, and 2C are electrical circuit diagrams of the device depicted in FIG. 1A.
Figure 2B:
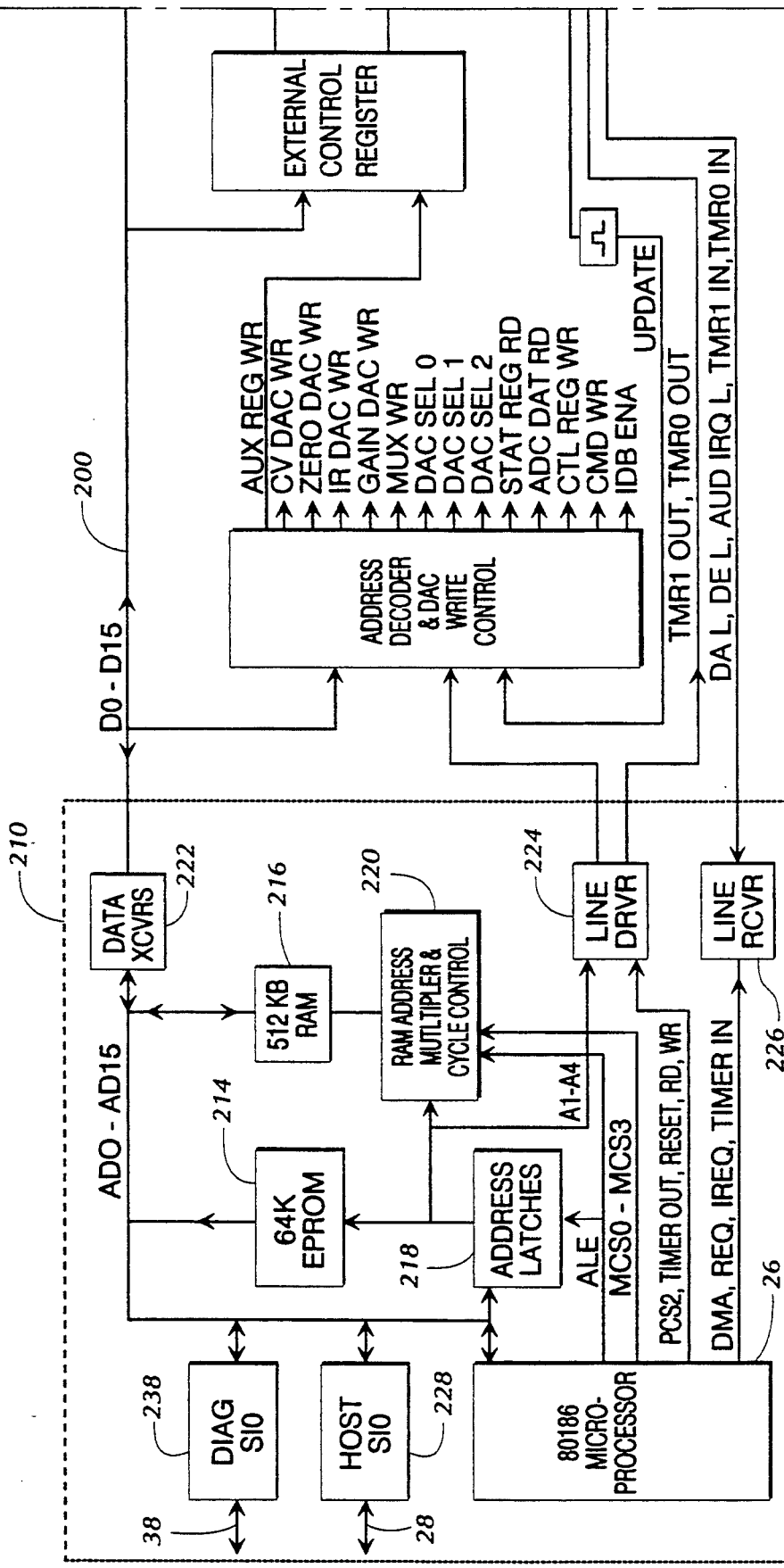
Figure 2C:
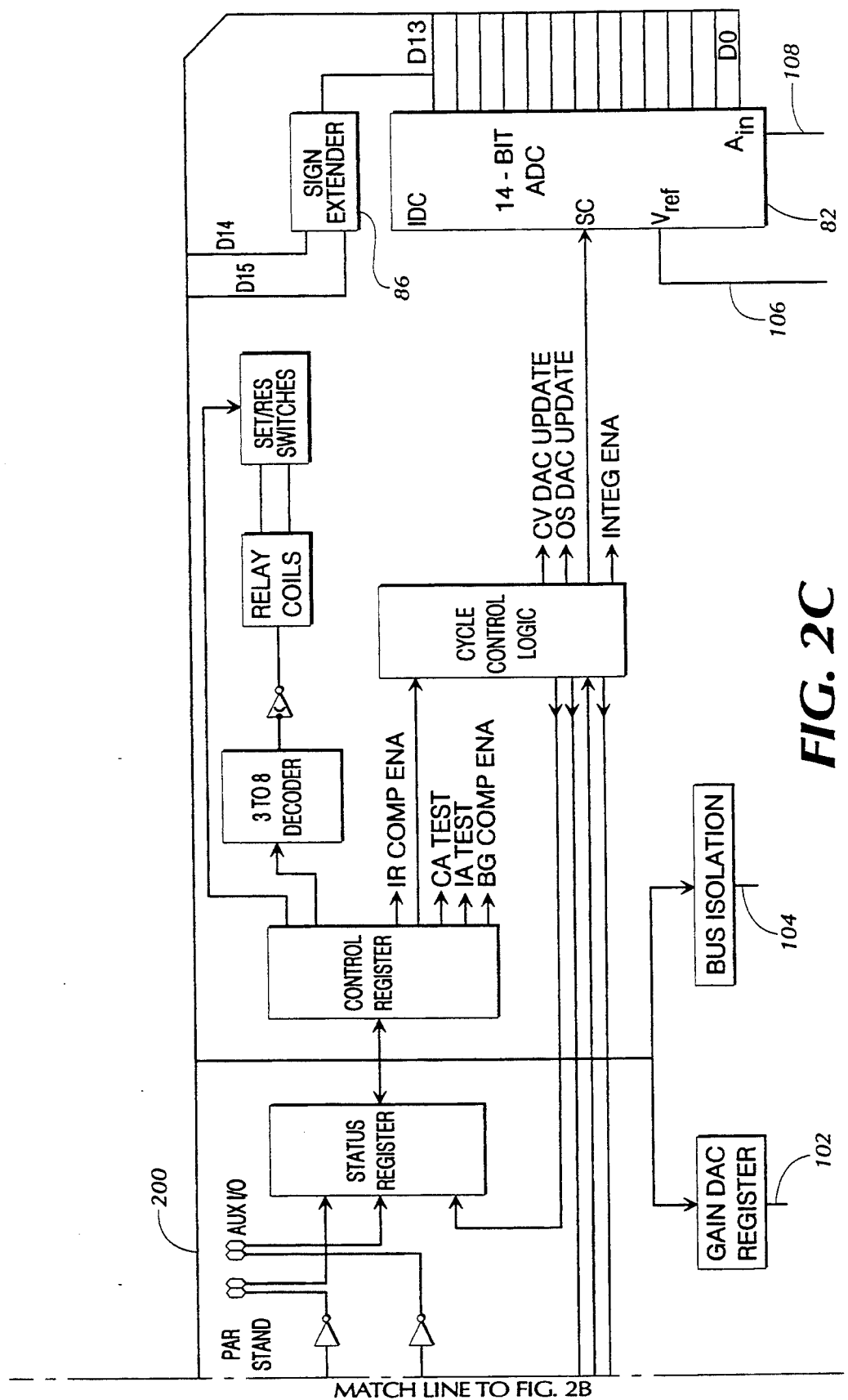

The basic circuit diagram of the digital instrument 10 is shown in FIGS. 2A, 2B and 2C. As indicated, the flow cell 14 comprises counter electrode 30, reference electrode 32 and working electrode 34. In this arrangement, the electrode to which potential is applied is the counter-electrode 30, the electrode which is used to monitor the cell voltage is called the reference electrode 32, and the electrode at which the cell current is measured is denominated the working electrode 34. The cell voltage is defined as the potential of the working electrode 34 with respect to the reference electrode 32 by voltammetric convention. However, in the preferred embodiment the working electrode 34 is maintained at virtual ground; therefore, when measured with respect to circuit ground, the cell voltage is the correct magnitude but of opposite sign. An alternate two-electrode configuration of the cell may be obtained by externally connecting the counter-electrode lead to the reference electrode lead and using a reference electrode that also serves as the counter electrode.

In one of the preferred embodiments, the cell voltage is supplied as a square wave superimposed on a linear voltage ramp. The linear ramp "sweeps" the cell voltage over the potential range of interest and the square wave enhances the steps in cell current, caused by oxidation or reduction of chemicals in the solution, by evaluating differences. Current measurements are made during each half-cycle of the square wave and the difference in the current of each half cycle of the square wave is calculated. This technique tends to cancel the dc components of cell current leaving the difference current of interest. The voltage and current characteristics so obtained permit the identification of various compounds in a solution and their respective concentrations.

The circuit which generates and maintains the cell voltage is, in voltammetric terms, referred to as potentiostat. This is a closed loop regulator which maintains the reference electrode 32 at a potential equal to the algebraic sum of all inputs to the potentiostat. The potentiostat 48 consists of operational amplifier 50 and operational amplifier 52 along with associated components. Operational amplifier 52 is preferably configured as a non-inverting, unity gain amplifier and isolates the reference electrode 32 from feedback resistor 54. Operational amplifier 50 sums inputs from the cell voltage DAC (digital-to-analog converter) 56, the positive feedback circuit via 8-bit DAC 46 and reference electrode 32, and generates a voltage at counter electrode 30 which makes the algebraic sum of all inputs to the potentiostat zero. DAC 56 actually contains two 16-bit converters with voltage outputs, which are used as the cell voltage and cell current offset (background compensation) sources. Cell voltage DAC 56 preferably has a full scale output of $+/-10$ V and is scaled through resistors 58, 60, and 62 to produce a maximum cell voltage of $+/-2$ V. The initial potential, cell voltage sweep and square wave half-cycles are generated by binary numbers written to the cell voltage DAC 56 via isolated data bus 100. An additional input to the summing point of operational amplifier 50 is provided through resistor 64. This input is not considered a potentiostat input since the purpose of this input is to cancel the offset errors of operational amplifier 50. Three latching relays 70 are also part of the potentiostat circuit. These relays isolate the cell 14 from the digital instrument 10 upon receipt of an appropriate control signal.

The cell current circuits convert the current detected by the working electrode 34 into a voltage, then amplify and integrate this voltage before it is digitized by analog-to-digital converter (ADC) 82, shown in FIG. 2C. This is a multi-stage process. In the first stage, current amplifier 80 converts the cell current to a voltage using a scale factor of 3.264 mA/V, 204 $\mu$A/V or 12.75 $\mu$A/V depending on the resistance in the feedback loop. These scale factors are in steps of 16 and selected by latching relays 132, 134. In the second stage, current amplifier 110 is preferably a digitally controlled gain stage providing an amplification of 2, 4, 8, 16, 32 or 64. This provides overall current to voltage conversion scale factors of 1.632 mA/V to 0.199 $\mu$A/V in overlapping steps of two. A multiplying CMOS DAC 92 is used as a digitally-controlled resistor in the feedback loop of current amplifier 110 to control amplifier gain. DAC 92 is operated from a $+15$ V supply (not shown) to provide a relative gain accuracy of approximately 0.005% ($\frac{1}{3}$ LSB). However, operating DAC 92 from $+15$ V makes the digital inputs incompatible with TTL logic levels; therefore, a TTL to CMOS level translator 94, is used. DAC 92 is operated in a non-latched mode and the gain control bits are latched in a 6-bit register. A CMOS switch 68 is used to ground the input of the amplifier stage when the amplifier offset error is being measured.

Amplifier 120 can be configured as an integrator or a unity gain inverting amplifier by relay 128. Four CMOS switches 112, 114, 116, and 118 are used in the integrator circuit, consisting of amplifier 120 and associated components. Two of these switches, 116 and 118, are used to enable or disable the integrator. The integrator is disabled by disconnecting switch 118 from the integrator input and resetting the integrator output to zero by shorting capacitor 122 via switch 116. The primary input to the integrator is the output of the second stage current amplifier 110. However, a second input from the offset or background compensation DAC 56 is algebraically added to the cell current input through switch 112 when background compensation is activated. In order to obtain an accurate representation of a response peak on either the voltage or time axis, it is necessary that a digital instrument be operated at gains sufficient to permit the peak to be represented by a large number of output levels of the analog-to-digital converter. Unfortunately, such high gains often result in the background exceeding the dynamic range of the instrument. The instrument 10 of the present invention has a unique feature which allows the background to be offset or compensated for by use of a background recorded previously at low gain. Then the gain can be increased to obtain the desired response for the peak period. Thus, the offset input is used to suppress a baseline cell current so the signal of interest can be amplified to a greater extent. In the preferred embodiment, operational amplifier 120 is configured as an integrator amplifier, and the offset input is used to bring the signal of interest within the +/−5 V range of the ADC 82, shown in FIG. 2C. Referring again to FIG. 2A, switch 114 is used to isolate operational amplifier 120 from the output of current amplifier 110 so that the offset error of operational amplifier 120 can be measured and appropriate compensation, applied through resistor 115, determined.

The device of FIGS. 2A, 2B, and 2C provides a means for automatic IR compensation. This feature is of particular importance when rapid pulse-type experiments in solutions of high resistance are performed. IR compensation is performed by a positive feedback circuit which is used to partially cancel the effect of "bulk" cell resistance between reference electrode 32 and working electrode 34, thereby enhancing the measured cell current. The objective of IR compensation is to add a voltage to the applied voltage which compensates for the voltage drop across uncompensated cell resistance. The positive feedback circuit includes a four-quadrant multiplying CMOS DAC 46 which allows the user to control positive feedback in terms of the ohmic value of uncompensated cell resistance. A range of 10 to 2550 ohms, in steps of 10 ohms, is provided by DAC 46 which is in effect a digitally controlled resistance between the feedback voltage source and the summing point of operational amplifier 50. The positive feedback source is selected by latching relays 132 and 134, which relays also determine the scale factor of the current to voltage converter, amplifier 80, so that appropriate compensation for the scale factor is provided. Positive feedback for the 204 μA/V and 12.75 μA/V ranges is derived using voltage dividers 136; however, the magnitude of the positive feedback voltage required on the 3.264 mA/V range is greater than the output of amplifier 80 and thus requires amplifier 90. IR compensation is enabled by the closing of CMOS switch 138.

The present invention also provides a means of allowing software routines to null amplifier errors in digital instrument 10. This function is provided by a quad 8 bit DAC 66 and a resistive summation network 76 which converts the 0 to +10 V outputs of DAC 66 to 0 to +/−100 mV sources used to null errors in operational amplifiers 120, 110, 50, and 80. The resistors of resistive summation network 76 are selected to provide worst case zero compensation for the amplifier stage and to maintain an integer relationship between DAC 66 and ADC 82 (shown in FIG. 2B) when used with the X16 amplifier, operational amplifier 150. Using an integer relationship between DAC 66 and ADC 82 allows the value at DAC 66 required to null amplifier errors to be calculated directly from the error voltage present at the amplifier's output.

ADC 82 is preferably a 14-bit, bipolar, 0 to +/−5 V analog-to-digital converter which is used to convert analog voltages to binary numbers in two's complement binary format. In this arrangement, the most significant bit is the sign bit and it is extended by sign extender 86 to provide a 16-bit signed number which is read by processor 210 of digital instrument 10 via direct memory access. ADC 82 requires +5 V, +12 V and −12 V supplies.

Relay 88 allows amplifier 150, configured for a non-inverting gain of 16, to be connected between analog multiplexer 84 and the analog input of ADC 82 at line 108. Amplifier 150 is used to improve the resolution of ADC 82 when sensitive measurements are to be made; e.g., when determining amplifier offset errors. Normal resolution of ADC 82 is approximately 0.61 mV/LSB and is improved to 38 μV/LSB by amplifier 150; however, the full scale analog to digital conversion value is correspondingly reduced to approximately +/−0.312 V.

Analog multiplexer 84 allows controller 210 of digital instrument 10 to connect any one of eight channels or inputs 96 to ADC 82. Typically, one channel of multiplexer 84 is grounded allowing the "zero" of ADC 82 or the ADC 82/amplifier 150 combination to be determined. This value can then be used by software in the controller 210 to correct other analog-to-digital conversion data if required. One channel of analog multiplexer 84 is connected to the output of DAC 56 via line 126 allowing DAC 56 to be used as a calibration source. The output of any amplifier in the potentiostat or current amplification stage can be selected with the other six channels 96 of analog multiplexer 84.

A +5 V internal reference voltage of ADC 82, shown at line 106, is used to provide reference voltages for the zeroing circuit as well as the zero and calibration potentiometers for DAC 56. Amplifier 140 provides a gain of 2 to generate the +10 V reference at line 74 which reference voltage is amplified by −1 by amplifier 130 to produce the −10 V reference at line 78.

Referring now to FIG. 2B, controller 210 is shown. Controller 210 is preferably a single board microcomputer which is, at the assembly language level, compatible with a 80286 based personal computer. Up to 128K bytes of firmware can be installed into EPROM 214 and 512K bytes of RAM 216 can be installed on controller 210. Two RS232 serial ports 28, 38, configured as data terminal equipment (DTE) are provided. Processor 26 is preferably an 80186 microprocessor with on-chip peripherals. Processor 26 uses a multiplex address/data bus controlled by RAM address multiplexer and cycle controller 220. Therefore, address latches 218 external to processor 26 must be used to hold the address during a read or write bus cycle. Address latches 218 preferably consist of three transparent 8-bit latches. Signals to and from the instrument board are buffered from the corresponding signals on the board for controller 210 by line drivers 224 and line receivers 226. Two EPROM's 214 are provided on controller 210 since the active data bus 200 is 16-bits wide. The address lines of EPROM 214 are directly driven by address latches 218 and the data output of EPROM 214 drive the address data bus.

Operation of the system of the present invention entails many tasks such as the precisely timed application of potentials, measurement of current responses, display and the storage of data as they are acquired, operation interface, and post-run analysis and display of results. It is not feasible to perform all of these tasks with a single digital processor. The post-run operations are preferably performed with a standard personal computer programmed with high-level languages. However, the drawback of such computers is that they are not well suited to the precise timing of potential applications and current measurements. Therefore, the present invention employs processor 26 of digital instrument 10 which is linked by serial interface 28 to host computer 12. The software used in conjunction with the system of the present invention is modular in nature. Digital instrument 10 contains a resident program (RPG) in EPROM 214. This program performs all system checks on power up, zeros the operational amplifiers via DAC 66, and establishes initial communication to host computer 12 via serial link 28. Error messages from RPG are sent to a diagnostic terminal port 38 for transmission to an optional diagnostic terminal via serial link 38. While normal operation does not require a diagnostic terminal, its use allows checking of many hardware features.

The operation of the system of the present invention during an experiment is handled by a pair of programs stored on hard disk 20 of host computer 12. To start an experiment using square-wave voltammerty, for example, an executable program is selected to be executed by the operating system of host computer 12. The executable program, which remains resident in the RAM of host computer 12 automatically downloads another executable program to the controller 210 of digital instrument 10. RPG receives the incoming executable program from host computer 12, loads it into RAM 216, and then rams over operation of controller 210 to the received executable program.

The next step in an experiment is the selection of parameters. The host-resident program displays a list of default values of the parameters and also displays the allowable ranges for selection by the operator. Activation of "Use These Parameters" on graphics display 18 results in the selected values being downloaded from host computer 12 to digital instrument 10. After entry of a name for the data file, the experiment starts. During an experiment, acquired data are transferred automatically from digital instrument 10 to the host computer 12, one sweep at a time, where they are checked for accuracy of transmission, stored in a file on hard disk 20, and displayed on graphics display 18.

During an experiment, the host-resident program displays the selected values of the experimental parameters below the data display. All of these parameters can be changed by the operator during the experiment except for the number of points in a sweep. When "Install" is selected on the parameter menu displayed on graphic display 18, a new set of parameters is downloaded to the digital instrument 10 and installed at the end of the next voltammetric sweep. Each set of parameters is saved in a file on hard disk 20 and each data sweep includes the parameter set number used for that sweep.

The set of parameters displayed during a run also includes a new parameter which is not available in the initial selection, "Base-line Compensation." When "Base-Line Compensation" is set to "Yes" and "install" selected, an ensemble average is made of the next four sweeps and saved as a base line. This base line is downloaded to digital instrument 10 and used to offset or compensate subsequent sweeps. The number of sweeps and the relative gain can be changed while the base-line compensation is active. If any of the other parameters is changed, the base-line compensation is turned off. If base-line compensation is desired, a new base line must be averaged and saved. An important purpose of the base-line compensation is to allow higher gain to be used in order to amplify response peaks and obtain more ADC levels in the data, i.e., the analyte of interest.

At any time during an experiment, entry of an ESC on keyboard 16 of host computer 12 results in termination of the run at the end of the present voltmetric sweep. After ESC, or normal completion, the data and parameter files are then closed and saved on hard disk 20 and the program returns to the initial parameter display showing the last values active during the run. A new experiment can be started immediately with the same parameters, or parameters can be changed. Entry of a second ESC returns the host computer 12 to the operating system.

Since data can be acquired at several gain levels during an experiment, it can be difficult to see the relative magnitudes of various peaks or to evaluate the effect of parameter changes. A post-run program, in the host computer is provided to normalize all data sweeps to one value of relative gain. The data of each sweep are normalized to the highest relative gain used in the experiment, unless that results in values exceeding the limit for a 16-bit signed integer. In that case, all values are divided by two.

The executable program in the digital instrument operates in a foreground-background mode. Hardware interrupts direct program control to one of four interrupt service routines for time-critical background operations. Upon completion of the time critical task, program control returns to the foreground loop. During an experiment, the primary foreground task is to transfer response data, one sweep at a time to the host computer 12 via the serial link 28.

Three of the four hardware interrupts occur in a set sequence and never overlap. An interrupt service routine is called after each potential change and loads the cell voltage DAC 56 with the next potential value. If background compensation is in use, the background compensation (also in DAC 56) is also loaded by this routine.

When the last response value for a sweep has been stored in RAM 216 via direct-memory access (DMA), the DMA count register goes to zero and triggers another hardware interrupt. This interrupt service routine then checks for hardware errors, sets the digital instrument 10 to standby mode, provides various housekeeping chores such as installing new potentials, offsets, or parameters, replaces the electrode drop, if a mercury electrode stand is in use, and starts a presweep delay timer.

When the presweep delay timer goes to zero, a third hardware interrupt service routine restarts the timers and returns the instrument to operate mode to start the next sweep. This routine also activates the current offset feature if its software flag is set.

A fourth hardware interrupt is triggered by reception of a character by the serial port. This interrupt is of lower priority and can be interrupted itself by any of the other three hardware interrupts. This interrupt calls an interrupt service routine which handles the reception of all communication from host computer 12. Transmission of information to the host PC is by polled mode rather than by interrupt mode. A system of acknowledge signals is used between the two processors so one does not attempt to transmit until the other is ready to receive. New potential tables, offset tables, and parameter sets are sent by the host computer to digital instrument 10 between data sweeps from digital instrument 10 to host computer 12.

In addition to sending data to host computer 12, the foreground program performs a number of tasks at the start of each experiment including installation of new interrupt vectors, zeroing of amplifiers, and initialization of numerous software flags and registers. During an experiment, the foreground program counts the number of sweeps performed and the number of data sweeps transmitted. Upon completion of potential sweeps, the digital instrument 10 is set to standby and all remaining data, if any, are transmitted to host computer 12.

The host-resident executable program also operates in a foreground-background mode but with only one hardware interrupt. The serial inputs/output port of the host computer, connected to serial link 28, causes a hardware interrupt when it receives a character from digital instrument 10. The host computer transmits information to digital instrument 10 in polled mode. A system of software signals such as acknowledge (ACK), not acknowledge (NAK), enquire (ENQ), cancel (CAN), and escape (ESC) are used between the host computer 10 and the digital instrument 10 and prevent transmission of data by one processor until the other processor is ready to receive.

The interrupt service routine screens incoming characters until a "data receive" software flag is set. Then, all characters are treated as response data and stored temporarily in a RAM buffer.

The main foreground program loop of host computer 12 is in operation during an experiment. At the start of the loop, it checks for a keyboard entry. If there is no keyboard entry, it then checks to see if a complete data sweep has been received. If the sweep is incomplete, it then checks to see if there are undisplayed sweeps in the data file and if so, displays the next sweep. If not, the program loops back to the start.

If a complete data sweep is available, the program verifies the checksum for the sweep, copies the data sweep to a data file, and increments the sweeps-in-file count so the data will be displayed on the next cycle through the loop.

If a keyboard entry was detected at the start of the loop, it is screened and an appropriate response generated. For example, an ESC will lead to termination of the experiment, an arrow key will move the cursor of the parameter display, and an "enter" will lead to a routine to change the parameter selected. If "enter" is struck on keyboard 16 while the cursor is at "install" on graphics display 18, a new set of parameters will be written to a parameter file and downloaded to digital instrument 10. If a new value for one of the potential parameters had been selected since the previous "install", then a new table of potentials will be calculated and downloaded to the instrument 10 before the new parameters are downloaded.

If "Base-Line Compensation" has been set to "yes" before "install", the response is more complex. Four complete response data sweeps must be received before any action is evident. These four sweeps undergo ensemble averaging and scaling and are then downloaded to the instrument 10 in advance of the new parameter set. The instrument 10 then uses these values to offset the base-line component of subsequent sweeps. If the relative gain is changed while the base-line compensation is selected, the averaged values for the base-line will be scaled up or down as needed. This allows increase in gain after the base line is compensated and leads to greatly improved definition of response peaks. If any of the parameters for potential, timing, or IR compensation are changed, base-line compensation will be turned off.

One of the notable features of the instrument system is the ability to change parameters during a run. This allows optimization of the parameter selection without having to terminate and restart the experiment, a feature of great importance when the instrument is serving as a detector for HPLC.

Figure 3A:
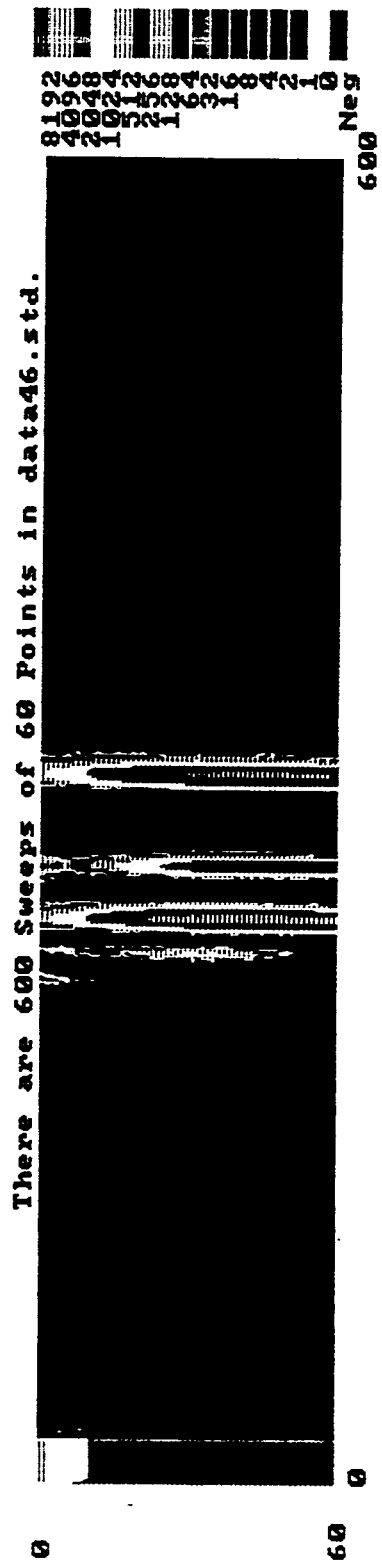
FIG. 3A is a graphical depiction of response data obtained during an experimental run using the instrument of the present invention.

During an experimental run, a sixteen-color display of response data appears as shown in FIG. 3A. The display appears as an array of illuminated pixels, one column for each voltammetric sweep with the first points at the top of the screen. Each successive voltammetric sweep is displayed, one pixel to the right of the previous sweep, until 600 sweeps are displayed. Then the display returns to the left side of the screen and starts a second array below the first one. If more than 1200 sweeps are acquired the display returns to the top of the screen and overwrites the display of the first sweeps.

The progression of colors is indicated by a color bar. Each successive color indicates a response magnitude double the previous one. This allows changes in background and minor peaks to be detected readily. After the experiment has been run and all the data saved, the acquired data may be processed by a normalization program. This program normalizes data values to a common relative gain setting. The program determines the highest gain setting that does not result in a value exceeding a 16-bit signed integer ($+/-32K$) and then scales all values to what they would have been if that gain setting had been used for their acquisition. These scaled or normalized values are then saved in a "normalized data" file. The purpose of the normalization is to present a more easily interpreted chromatogram which does not show discontinuities resulting from changes of gain during the run.

Figure 3B:
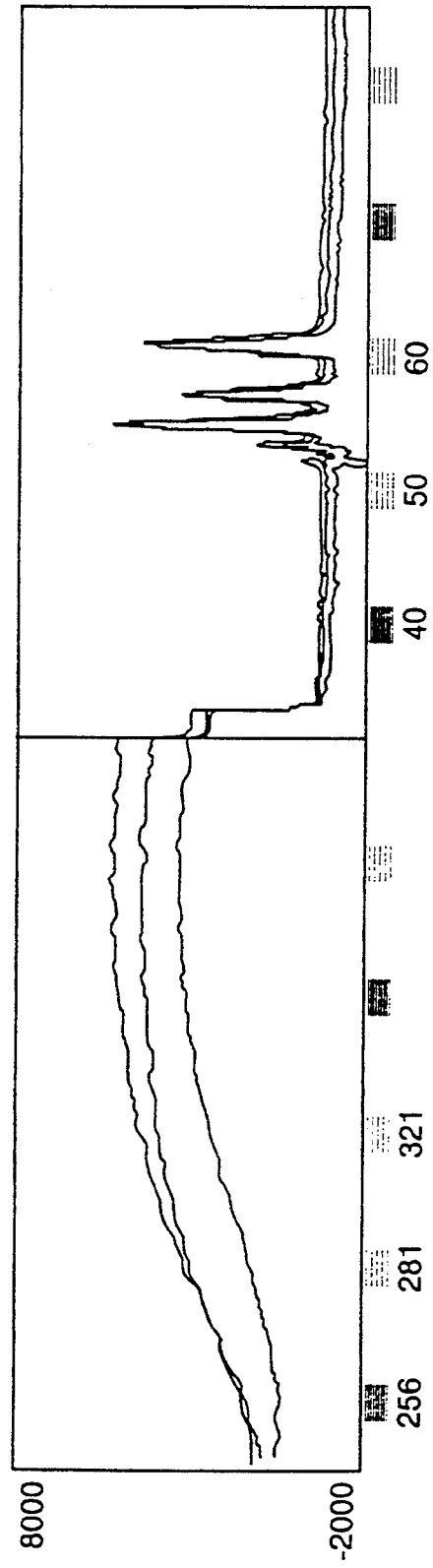
FIG. 3B is a graphical depiction of a voltammogram and a chromatogram for a point selected from the data of FIG. 3A.

Another computer program permits one to display and analyze data obtained by the instrument. This program requires a computer with a mouse, an EGA monitor, and at least 256K of video RAM. A hard disk is not necessary, but results in faster program execution. After entering the name of the data file, the data are displayed on graphics display 18 in a color-contour plot as depicted in FIG. 3A, which is similar to that displayed during data acquisition. Points on this display can then be selected by clicking the left button of the mouse. For each point selected (maximum of five at one time) a voltammogram and chromatogram are displayed in small view ports at the bottom of graphics display 18 as shown in FIG. 3B. These small displays can be cleared and other points selected, or the voltammograms and chromatograms can be selected, one at a time, for an enlarged display on a second screen as shown in FIGS. 4 and 5, respectively.

Figure 4:
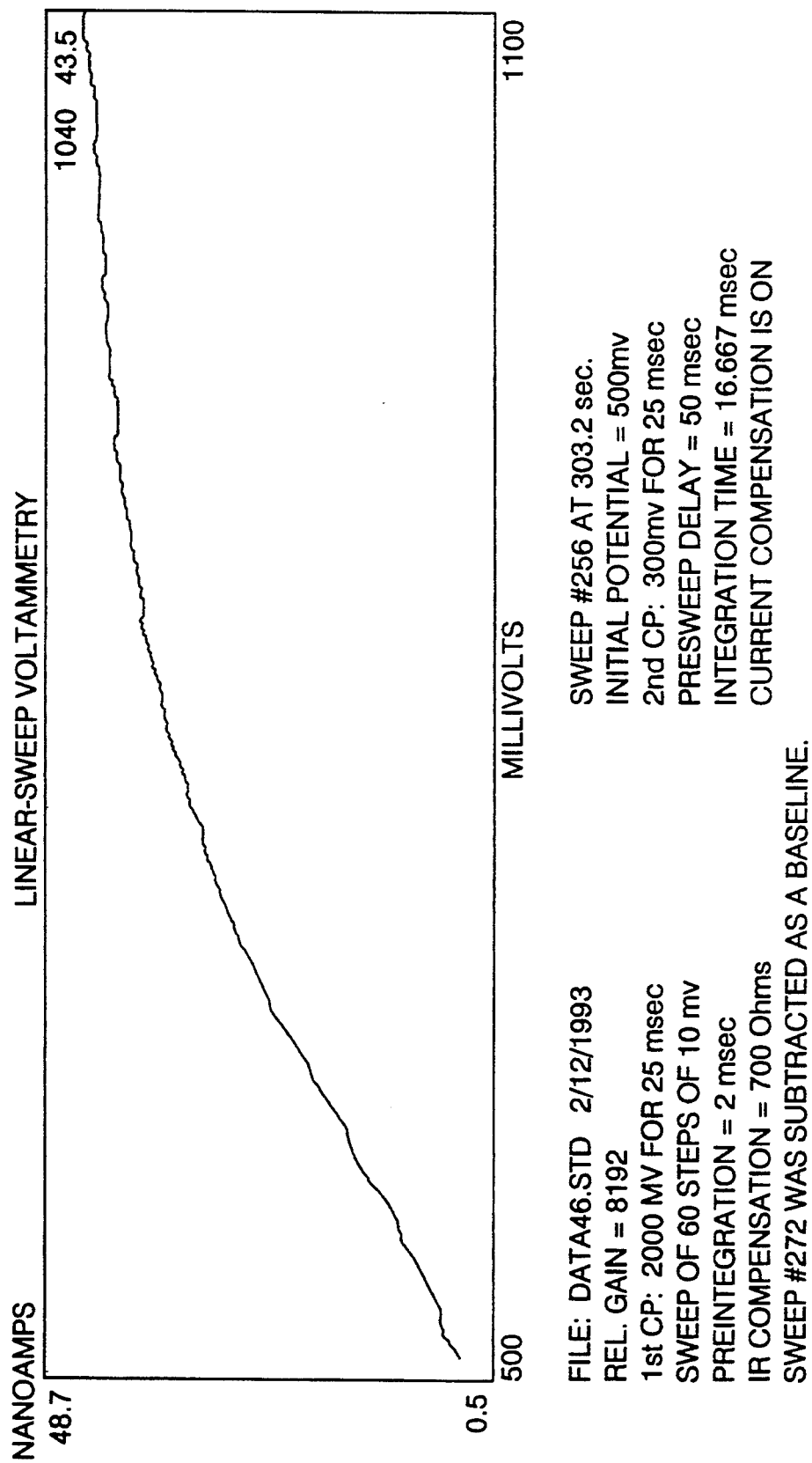
FIG. 4 is an enlargement of a portion of the voltammogram of FIG. 3B.

Enlarged voltammograms, as shown in FIG. 4, are identified by technique, file name, date of file creation, sweep number, experiment time to the start of the sweep, and a complete list of experimental parameters used for that voltammetric sweep. The horizontal axis is given in millivolts, and the vertical axis is given in nanoamperes. Points on the voltammogram, selected by mouse, are labeled with potential and current. This display can be dumped to a printer to yield a copy for a research notebook.

Figure 5:
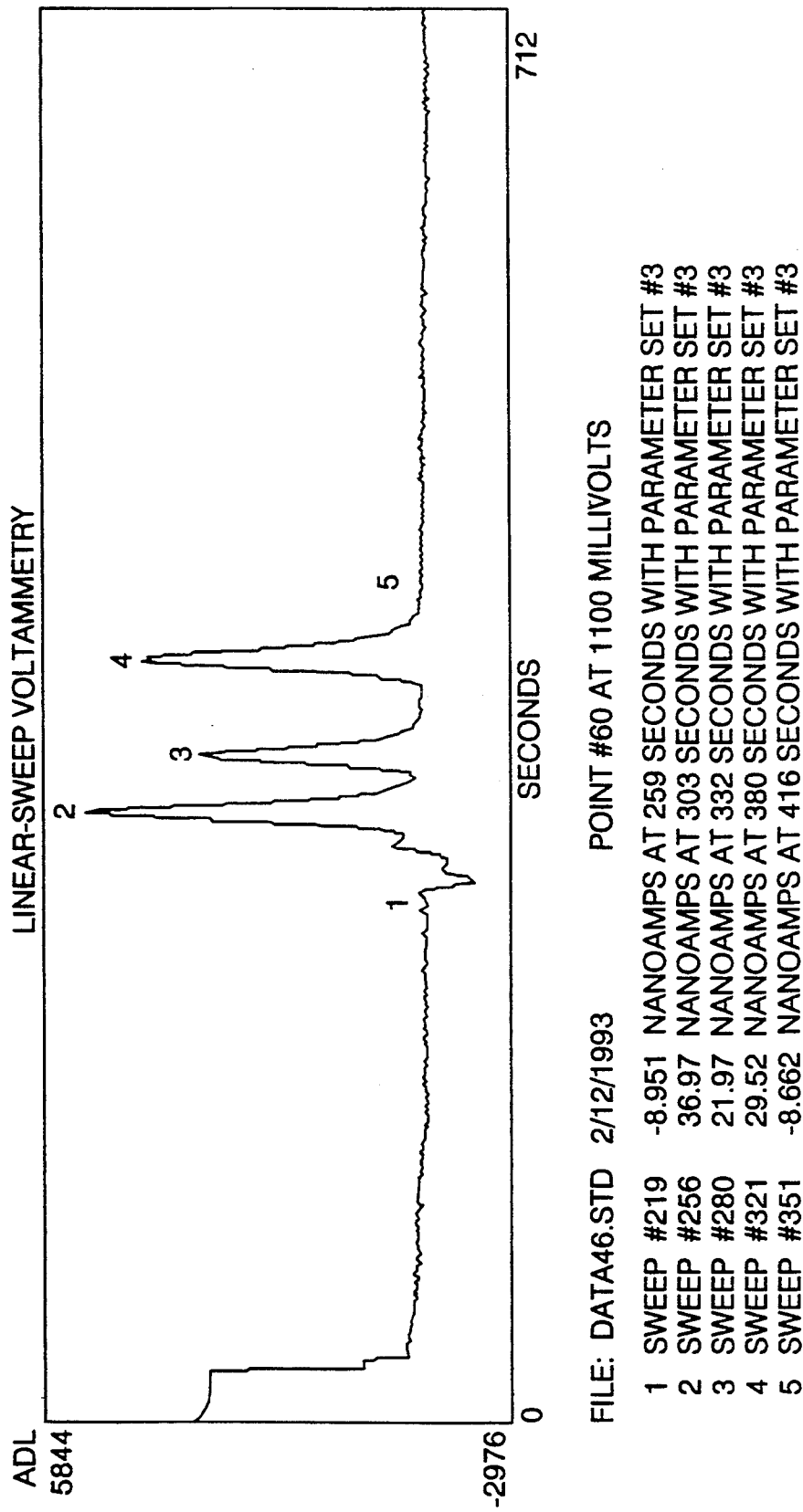
FIG. 5 is an enlargement of a portion of the chromatogram of FIG. 3B.

Enlarged chromatograms, as shown in FIG. 5, are identified by technique, file name, date of file creation, and sweep point number. The horizontal axis is given in seconds, and the vertical axis, in ADC levels. This latter is necessary since the conversion to current depends on several parameters which can be changed during an experiment. Points on the chromatogram, selected by mouse, result in a tabular listing below the plot giving sweep number, current, and time at the start of that sweep. This display can be dumped to a printer to yield a copy for a research notebook.

Figure 6:
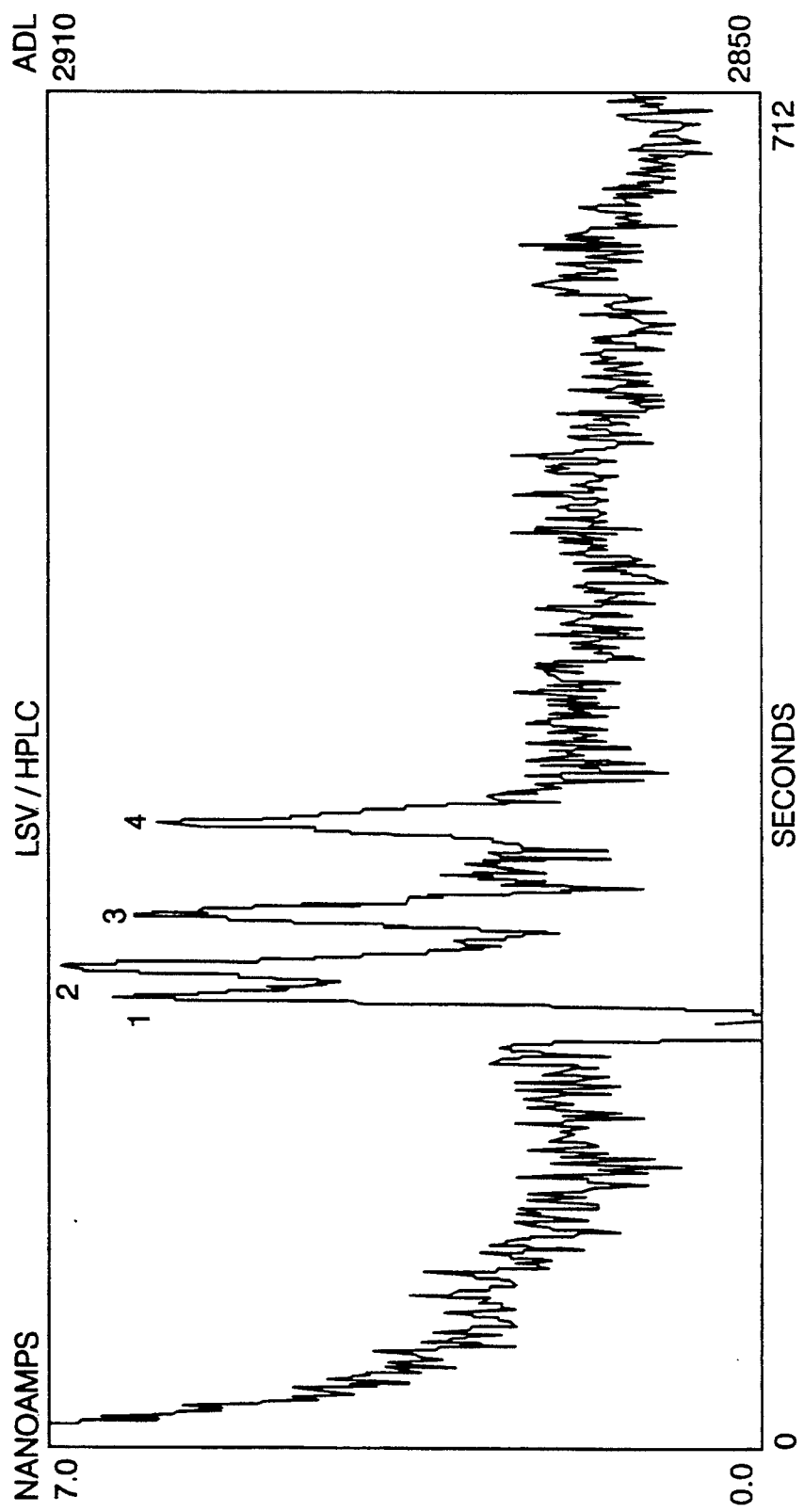
FIG. 6 is a graphical depiction of an experimental run using the device of the present invention with the background compensation feature deactivated.
Figure 7:
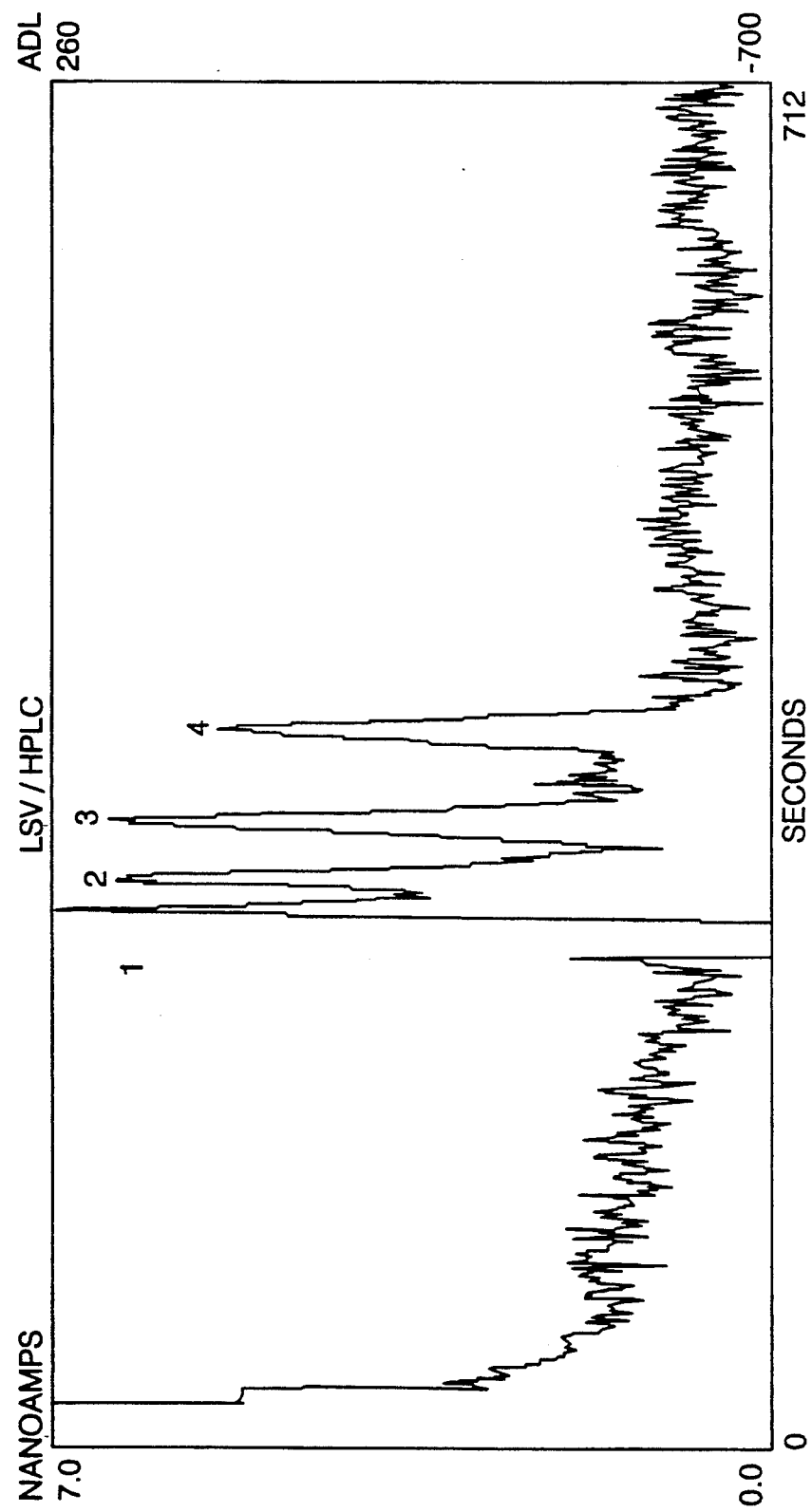
FIG. 7 shows a repeat of the experimental run of FIG. 6 with the background compensation feature of the present invention activated.

FIGS. 6 and 7 show graphical depictions of the data obtainable with the instrument of the present invention. The results shown illustrate the peaks associated with a mixture of various catecholamines. FIG. 6 illustrates the results obtained when the background compensation feature of the present invention is not activated. As shown, only 60 levels of ADC 82 are available to display the data. By contrast, FIG. 7 shows the same run with the background compensation feature activated. As shown, 960 levels of ADC 82 are available to display results. This broad dynamic response range is permitted because of the increased gains possible when background compensation is used.

The results shown in FIGS. 6 and 7 were obtained using a solvent of 95% 0.05 m citrate buffer with a pH of 5.2 and 5% acetonitrile with a flow rate of 0.8 ml/min. In FIGS. 6 and 7, peak 1 represents the solvent front, peak 2 represents 4.9 ng norepinephrine and peak 3 represents 4.88 ng epinephrine. Peak 4 was produced by dopamine (4.30 ng).

While the invention has been disclosed in preferred forms, it will be readily apparent to those skilled in the art that many modifications, additions, and deletions may be made therein without departing from the spirit and scope of the invention as set forth in the appended claims.

What is claimed is:

1. A voltammetric instrument for determining the concentration of at least one analyte in a solution in the presence of background values based on the current-/voltage characteristics of the solution, comprising:
   (a) two electrodes for immersion in the solution;
   (b) generator means connected to said electrodes for applying non-constant voltages at said electrodes;
   (c) sensing means for measuring currents at said electrodes in response to the voltages applied at said electrodes to establish analog composite values of the solution;
   (d) compensation means for offsetting the analog composite values of the solution by background values of the solution to obtain compensated analog values of the analyte; and
   (e) analog-to-digital converter means for converting the compensated analog values to compensated digital values for output.

2. The instrument of claim 1 further comprising an internal microprocessor with at least one port for connection to a host computer.

3. The instrument of claim 1 wherein said compensation means comprises means for storing the background values of the solution.

4. The instrument of claim 1 wherein said compensation means comprises electronic combining means for combining the analog composite values of the solution and the background values.

5. The instrument of claim 4 wherein said electronic combining means comprises an integrator.

6. The instrument of claim 1 further comprising a third electrode for monitoring the voltage of the solution.

7. The instrument of claim 1 wherein the background values are overtime.

8. The instrument of claim 1 wherein said generator means is adapted to generate and maintain voltages which are square-waves superimposed on linear voltage ramps.

9. The instrument of claim 8 wherein said sensing means determines the current at said electrodes during each half-cycle of said square-wave voltages.

10. The instrument of claim 1 wherein the background values are scaled to provide for background compensation of new experimental measurements made at increased amplification.

11. A method of determining a concentration of at least one analyte in a solution, comprising the steps of:
   measuring background values for the solution with a measuring instrument;
   storing the background values in the measuring instrument;
   measuring analog composite values of the solution with the measuring instrument; and
   combining, in the measuring instrument, the background values and the analog composite values of the solution in a manner to offset the analog composite values of the solution by the background values to obtain compensated values of the analyte representative of the concentration of the analyte in the solution.

12. The method of claim 11 wherein the background values are over time.

13. The method of claim 11 further comprising the step of determining the current/voltage characteristics of the solution.

14. The method of claim 11 further comprising the step of scaling the background values to provide for background compensation of new experimental measurements made at increased amplification.

15. The method as claimed in claim 11 wherein the compensated values of the analyte are analog, further comprising the steps of converting the analog compensated values to digital compensated values and passing the digital compensated value to an external computer.

16. In a voltammetric measuring instrument of the type for measuring the concentration at least one analyte in a solution and having an analog-to-digital converter for converting analog signals to digital form for passing digital signals to an external computer, the improvement therein comprising:
   multi-channel background compensation means for removing analog background values of the solution from analog composite values of the solution to establish compensated analog values of the analyte in preparation of passing the compensated analog values to the analog-to-digital converter.

17. The improvement of claim 16 wherein said background compensation means comprises electronic combining means for establishing a net difference between the analog background values and the composite analog values of the solution.

* * * * *